(12) United States Patent
Jefferies et al.

(10) Patent No.: US 7,976,850 B2
(45) Date of Patent: Jul. 12, 2011

(54) POX VIRIDAE TREATMENT

(75) Inventors: Wilfred Arthur Jefferies, Surrey (CA);
Timothy Z. Vitalis, Vancouver (CA);
Quian-Jin Zhang, Richmond (CA);
Judi Barbara Alimonti, Winnipeg (CA);
Susan Shu-Ping Chen, Vancouver (CA);
Genc Basha, Vancouver (CA); Kyung Bok Choi, Vancouver (CA)

(73) Assignee: Tapimmune, Inc., Seattle, WA (US)

( * ) Notice: Subject to any disclaimer, the term of this patent is extended or adjusted under 35 U.S.C. 154(b) by 21 days.

(21) Appl. No.: 12/474,331

(22) Filed: May 29, 2009

(65) Prior Publication Data
US 2010/0303894 A1    Dec. 2, 2010

Related U.S. Application Data

(63) Continuation of application No. PCT/CA2006/001945, filed on Nov. 30, 2006.

(51) Int. Cl.
*A61K 39/275* (2006.01)
*A61K 9/14* (2006.01)
*A61K 9/50* (2006.01)

(52) U.S. Cl. .................. 424/232.1; 424/278.1; 424/489

(58) Field of Classification Search ........................ None
See application file for complete search history.

(56) References Cited

U.S. PATENT DOCUMENTS

| 4,399,216 A | 8/1983 | Axel et al. |
| 4,704,362 A | 11/1987 | Itakura et al. |
| 4,766,950 A | 8/1988 | Yamada et al. |
| 4,784,950 A | 11/1988 | Hagen et al. |
| 4,801,542 A | 1/1989 | Murray et al. |
| 4,935,349 A | 6/1990 | McKnight et al. |
| 5,034,506 A | 7/1991 | Summerton et al. |
| 5,843,456 A | 12/1998 | Paoletti et al. |
| 2003/0082195 A1 * | 5/2003 | Jefferies et al. ............ 424/184.1 |

FOREIGN PATENT DOCUMENTS

| WO | W09204033 A1 | 3/1992 |
| WO | WO 2004/112706 | * 12/2004 |

OTHER PUBLICATIONS

Vitalis et al (PLOS Pathogens 1(4) e36, Dec. 2005).*
Deverson, E. V. et al., "MHC class II region encoding proteins related to the multidrug resistance family of transmembrane transporters", Nature Dec. 20-27, 1990; 348(6303): 674-5—Abstract.
Trowsdale, J. et al., "Sequence encoded in the class II region of the MHC related to the 'ABC' superfamily of transporters", Nature Dec. 20-27, 1990, 348(6303):674-5—Abstract.

* cited by examiner

*Primary Examiner* — Mary E Mosher
(74) *Attorney, Agent, or Firm* — Rissman Hendricks & Oliverio LLP

(57) ABSTRACT

A vaccine composition for combating *Pox viridae* viral infections in living organisms such as mammals (including humans) comprises TAP-1 and/or TAP-2 to augment the antigen processing capability of infected cells and hence their immunogenicity. The composition may be used alone or, preferably, as an immunogenicity-enhancing adjuvant with a pox antigen-based vaccine, especially in the treatment or prophylaxis of viral infections such as smallpox.

1 Claim, 8 Drawing Sheets

POX VIRIDAE TREATMENT

CROSS-REFERENCE TO RELATED APPLICATIONS

This application is a continuation of PCT application PCT/CA2006/001945, filed Nov. 30, 2006, the disclosure of which is incorporated by reference herein in its entirety.

BACKGROUND OF THE INVENTION

This invention relates to vaccines, vaccine compositions, methods of preparation of vaccines, and uses thereof in the prophylaxis and treatment of viral infections in mammalian patients (including humans). More specifically it relates to vaccines and vaccine compositions useful in combating a virus of the family *Pox viridae*, such as vaccinia virus ("VV") and smallpox virus.

Vaccines against *Pox viridae* viruses, especially VV and small pox, are known, and have been used for many years with a large degree of success. However, adverse responses to standard doses of inocula is a problem quite frequently encountered in vaccination against VV and small pox. As a result, conventional vaccines cannot be administered to a significant fraction of the population who are either immune suppressed or who would otherwise react adversely to the establish vaccine protocols. This can amount to as many as 20% of the individuals targeted to be inoculated. More efficient inocula compositions, allowing smaller effective does, would be a significant advantage in this respect. Ineffectively vaccinated patients pose a severe threat of spread of the infectious disease As vaccination against a variety of pathogens becomes more widespread, needs develop to increase the efficiency of the inocula, while reducing the sizes of the batches of vaccine required for vaccination of an entire population. This is particularly important during times of acute need (bio-terrorist attacks, emergent epidemic, for example) when rapid responses are required.

To increase vaccine potency and efficiency, a variety of adjuvants have been developed. These include Freund's complete adjuvant (FCA) which is an emulsion containing heat killed *mycobacterium tuberculosis*, which has proved to be too toxic for use in humans; cytokines such as IL-2 and IL-12, which elicit a Th-I response conducive to cytotoxic mechanisms in the immune system; and oil emulsion/aluminum salts containing immune stimulators (proinflammatory bacterial products). Many of these are too toxic for use in humans. Others cannot be implemented because their mode of action is obscure.

Preferred, effective vaccines and vaccine-adjuvant combinations should elicit both a humoral response and a cell mediated response in the mammalian subject. The humoral response causes the raising of antibodies specific to the antigens of the invading pathogen and results in lasting defense against future invasions of the same pathogen. The cell mediated response involves destruction of infected cells by killer T-cells, i.e. cytotoxic T-lymphocytes ("CTLs").

It is known that the cytotoxic T-lymphocyte cell (CTL) response is a major component of the immune system, active in immune surveillance and destruction of infected cells and invading organisms expressing foreign antigen on their surface. A peptide fragment of the antigen binds to major histocompatiblity complex molecules (MHC) to form the ligand of the antigen specific T-cell receptor. Cytotoxic T-lymphocytes recognize peptide bound to MHC Class 1 molecules on the surface of the infected cells, and destroy them. For this to occur, a ternary complex must be formed in the cell and transported to the cell surface. The formation of the ternary complex is thought to involve the transport of peptides, generated by protein degradation in the cytoplasm of the cell, into the lumen of the endoplasmic reticulum (ER). This transport involves two genes located in the MHC region which encode proteins of the ATP binding cassette (ABC) family, call TAP-I and TAP-2 (Deverson, E. V. et al, "Nature" 348:738, 1990).

SUMMARY OF THE INVENTION

The present invention is based upon the discovery that augmenting the presence of TAP-I or TAP-2 in a *Pox viridae* virally infected cell, e.g. by enhancing TAP expression in the cell, substantially increases the MHC Class 1-antigen presentation of the cells so as to effect a substantial increase in immogenicity of the infected cells. This manifests itself in a substantially increased cytotoxic T-lymphocyte response and consequent increased destruction of the infected cell by the CTL.

Thus according to one aspect of the present invention, there is provided a vaccine composition for the treatment or prophylaxis of *Pox viridae* infections in living organisms, comprising TAP-I and/or TAP-2, or precursors thereof. As used herein, "TAP" is an abbreviation for "transporters associated with antigen processing".

According to another aspect, the invention provides an adjuvant for administration to a living organism for the treatment or prophylaxis of *Pox viridae* infections in conjunction with a *Pox viridae* viral vaccine containing live or attenuated *Pox viridae* virus, the adjuvant comprising a pharmaceutically acceptable composition comprising TAP-I and/or TAP-2, or precursors thereof.

A further aspect of the present invention provides a method of treatment or prophylaxis of a living organism to combat *Pox viridae* infections, which comprises administering to the patient an effective amount of a pharmaceutically acceptable composition comprising TAP-I and/or TAP-2, or precursors thereof optionally in conjunction with a *Pox viridae* viral vaccine containing live or attenuated *Pox viridae* virus.

The invention also provides, from another aspect, the preparation or manufacture of a pharmaceutical composition for the treatment or prophylaxis of *Pox viridae* infections in living organisms, the composition comprising TAP-I and/or TAP-2, or percursors thereof.

BRIEF REFERENCE TO THE DRAWINGS

Figure 8:
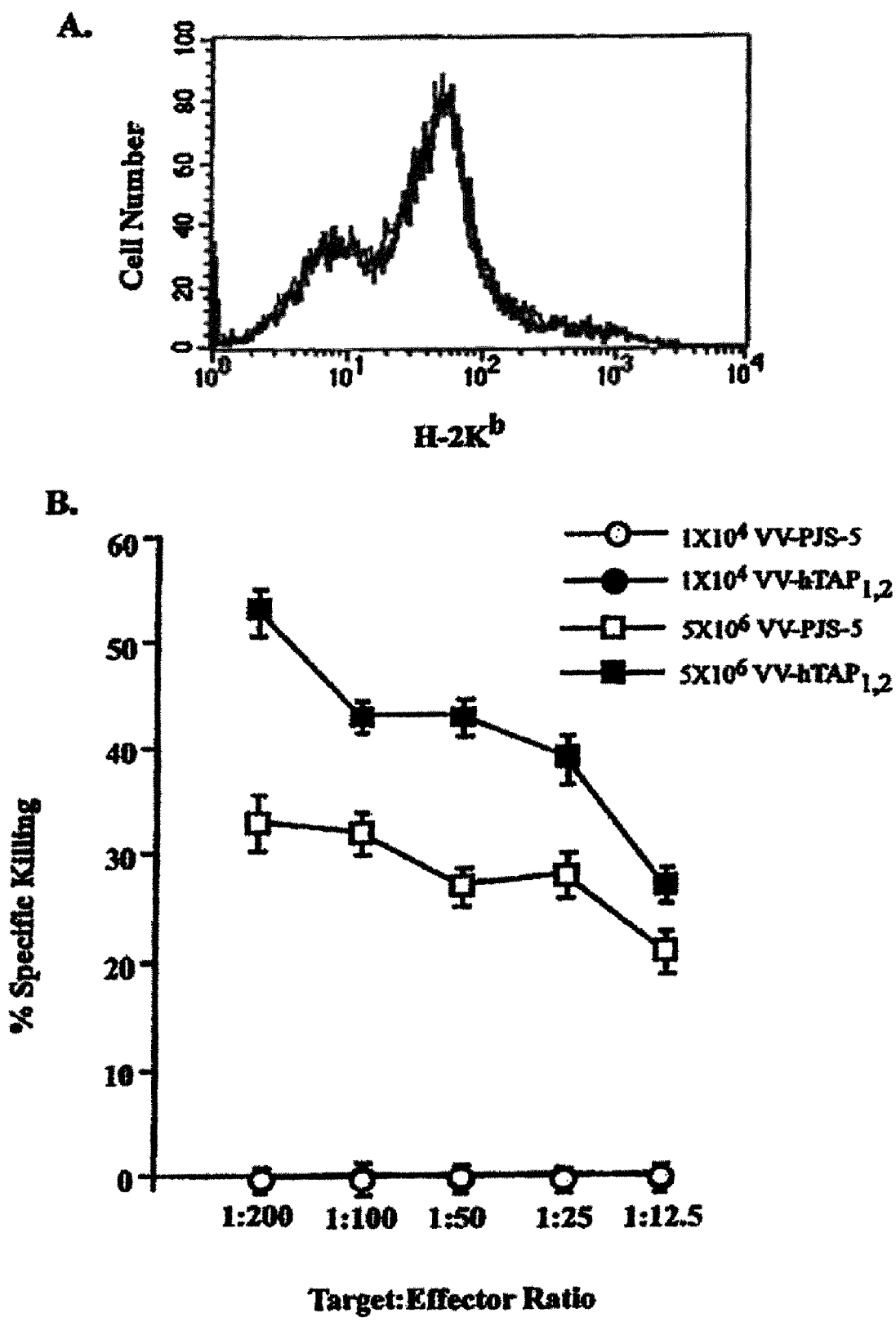

FIGS. 8*a* and 8*b* are graphical representations of the results of experiments shown in Example 7 below.

DESCRIPTION OF THE PREFERRED EMBODIMENTS

The over-expression of TAP, or the presence of excess TAP, in living organisms, in proper functional relationship with an antigen of a *Pox viridae* virus in a cell capable of presenting the antigen, increases antigen presentation, and therefore enhances antigen specific cytotoxicity in response to a *Pox viridae* viral infection. The TAP-I and/or TAP-2 protein may be generated in situ in the living mammalian cells, or may be introduced into the cells as a preformed protein, in any manner which ensures that at least some of the TAP protein(s)

enter into and participate in the antigen presenting pathway of the cell. A preferred way of causing the participation of TAP in the antigen presenting pathway of the cells is to arrange TAP over-expression therein, e.g. by administration to the living organism an expression system carrying TAP-I and/or TAP-2 genes, which expresses TAP in the cells.

Accordingly, preferred vaccine compositions of the present invention comprise one or both of the TAP-I or TAP-2 genes, in expressible form, for injection into a *Pox viridae* infected living organism or a living organism at risk of similar infection. The TAP-I and TAP-2 genes are suitably provided as components of a recombinant viral vector such as a vaccinia viral vector, or adenohuman viral vector along with an appropriate promoter, signal and expression sequences, so that after injection as a vaccine itself, or as a vaccine adjuvant along with a live or attenuated pox antigen-containing vaccine, TAP-I and/or TAP-2 is thus over-expressed in the antigen presenting cells. This significantly increases the output of the antigen presentation pathway, by increasing the activity of these transporters. TAP over-expression can act as an adjuvant for increasing responses against *Pox viridae* virus, especially smallpox virus, in immuno-competent and immuno-compromised hosts.

Another way of practicing the present invention is the preparation and administration to living organisms of a naked DNA plasmid coding for the TAP-I and/or the TAP-2 gene, along with the antigen against which immunity is to be developed, e.g. smallpox antigen. The antigen may be encoded in the DNA plasmid for expression in cells of the organism after administration, or added to the cells as a separate entity from the TAP-encoding plasmid.

In the alternative, the TAP-I and/or TAP-2 proteins themselves, expression products of the TAP-I and TAP-2 genes, and obtainable by cell cultivation techniques and in other ways can be used directly as a vaccine or vaccine adjuvant. When the TAP protein(s) themselves are used, alone or as an adjuvant with a pox virus-based vaccine, they should be administered in a form facilitating their entry into the cells. One suitable such way is administration of the proteins encapsulated in liposomes. Techniques for accomplishing this are known in the art.

The viral antigen to which the immune response is to be generated in accordance with the invention is preferably smallpox virus, since this is the commonest, most serious viral infection of members of the *Pox viridae* family. However, it is applicable to other members of the *Pox viridae* family which includes the subfamilies Chordopoxvirinae and Entomopoxvirinae. The subfamily Chordopoxvirinae includes the genuses: variola virus (smallpox virus); avipoxvirus (which includes species canary poxvirus; fowl pox virus; Hawaiian goose poxvirus; pigeon pox virus; and vulture gryphus poxvirus); capripoxvirus (which includes species capripoxvirus strain Rapine; goat pox virus; lumpy skin disease virus; and sheep pox virus); leporipoxvirus (which includes species malignant rabbit fibroma virus; myxoma virus; rabbit fibroma virus and Shope fibroma virus); molluscipoxvirus (which includes species molluscum contagiosum virus); orthopoxvirus (which includes species aracatuba virus; BeAn 58058 virus; Buffalo pox virus; camel pox virus; cantagalo orthopoxvirus; cowpox virus; ectromelia virus; elephant pox virus; monkey pox virus; rabbit pox virus; raccoon pox virus; skunk pox virus; tarapox virus; vaccinia virus; and volepox virus); parapoxvirus (which includes species bovine popular stomatitis virus; orf virus; pseudocowpox virus; red deer parapoxvirus; and seal pox virus); suipoxvirus (which includes species swinepox virus) and yatapoxvirus (which includes species tanapox virus; yaba monkey tumor virus; and yaba-like disease virus).

Thus, the present invention relates to the treatment of viral infections in living organisms infected with any of the above viruses, the living organism being a mammal (including humans), a bird or any other organism in which the virus is a natural infectant or to which it has transfected. It also relates to prophylaxis against the spread of such infections in any of these living organisms.

When the method of the invention is used in a prophylactic therapy or a vaccine, the target cell is essentially a normal cell (expressing normal TAP levels) that may not have been otherwise exposed to the pox antigen. In such a case, the agent that augments TAP is coadministered with the pox antigen to which one wishes to generate an immune response. Substantially all of the *Pox viridae* viral species listed above are sufficiently similar to smallpox virus that vaccination with any of them, accompanied by TAP over-expression in the antigen-presenting cells, will confer an effective degree of immunity against smallpox on the treated organism. When the method of the invention is used as a therapeutic, the target cell may be previously infected with pox virus.

A particularly preferred use of the present invention is in connection with the strain of vaccinia known as Modified Vaccinia Ankara (MVA), which is an attenuated strain of vaccinia and was used in the late stages of the smallpox eradication program undertaken by Western government authorities in the late 1970s. This has a superior safety profile, but a lower degree of immunogenicity than the widely commercially used "dryvax" strain. Increasing the immunogenicity of MVA by use in combination with TAP and TAP expression systems in accordance with the present invention, without detracting from its very good safety profile, has the potential to provide a superior smallpox vaccine for human patients, especially immunocompromised such patients.

In a preferred embodiment, the method of the invention involves administering a recombinant viral vector, which comprises a nucleic acid molecule, encoding a TAP molecule in order to augment the level of TAP expression in the target cell. Thus in one preferred embodiment, the present invention provides a method of enhancing an immune response to a pox antigen comprising administering an effective amount of a nucleic acid molecule comprising a sequence encoding a TAP molecule in expressible form to a living organism such as a mammal in need thereof.

The nucleic acid molecule encoding the TAP molecule can be administered to the animal in vivo where the TAP molecule will be expressed in vivo. When administered in vivo, the TAP molecule can be administered by any route including, but not limited to, intraperitoneally, intravenously, subcutaneously, orally, scarfocially, intramuscularly or intradermally. As an alternative, the TAP molecule can be administered to the target cells ex vivo where the TAP molecule will be expressed in the cells in vitro and then the target cells expressing TAP can be administered to the animal.

The nucleic acid molecule comprising a sequence encoding TAP-1 and/or TAP-2 under the control of a suitable promoter may be readily synthesized using techniques known in the art. A sequence encoding TAP-1 includes a sequence encoding a protein having the amino acid sequence as set out in Trowsdale, J. et al., *Nature* 348:741, 1990 and international Patent Application No. PCT/US91/06105 published on Mar. 19, 1992. A nucleic acid molecule comprising a sequence encoding TAP-1 may be isolated and sequenced, for example, by synthesizing cDNA's from RNA using rapid amplification of cDNA ends (*RACE*, Frohman, et al., 1986) using oligonucleotides specific for TAP-1 and analyzing the sequences of the clones obtained following amplification. Oligonucleotides specific for TAP-1 may be identified by comparing the nucleic acid sequence of the nucleic acid molecules of the invention to known sequences of TAP-1. Nucleic acid molecules used in the method of the invention encoding TAP-1 or Tap-2 may also be constructed by chemical synthesis and enzymatic ligation reactions using procedures known in the art. The sequence encoding TAP-1 or TAP-2 may also be prepared using recombinant DNA methods.

The method of the invention not only contemplates the use of the known TAP-1 and TAP-2 sequences, but also includes the use of sequences that have substantial sequence homology to the known TAP sequences, sequences that hybridize to the known TAP sequences, as well as all analogs or modified forms of the known TAP sequences. The term "sequence that has substantial sequence homology" means those nucleic acid sequences which have slight or inconsequential sequence variations from the known TAP sequences i.e., the sequences function in substantially the same manner and can be used to augment an immune response. The variations may be attributable to local mutations or structural modifications. Nucleic acid sequences having substantial homology include nucleic acid sequences having at least 65%, more preferably at least 85%, and most preferably 90-95% identity with the known nucleic acid sequences of TAP.

The term "sequence that hybridizes" means a nucleic acid sequence that can hybridize to a TAP sequence under stringent hybridization conditions. Appropriate "stringent hybridization conditions" which promote DNA hybridization are known to those skilled in the art, or may be found in *Current Protocols in Molecular Biology*, John Wiley & Sons, N.Y. (1989), 6.3.1-6.3.6. For example, the following may be employed: 6.0× sodium chloride/sodium citrate (SSC) at about 45° C., followed by a wash of 2.0×SSC at 50° C.; 0.2×SSC at 50° C. to 65° C.; or 2.0×SSC at 44° C. to 50° C. The stringency may be selected based on the conditions used in the wash step. For example, the salt concentration in the wash step can be selected from a high stringency of about 0.2×SSC at 50° C. In addition, the temperature in the wash step can be at high stringency conditions, at about 65° C.

The term "a nucleic acid sequence which is an analog" means a nucleic acid sequence which has been modified as compared to the known sequence of a TAP molecule wherein the modification does not alter the utility of the sequence as described herein. The modified sequence or analog may have improved properties over the known sequence. One example of a modification to prepare an analog is to replace one of the naturally occurring bases (i.e. adenine, quinine, cytosine or thymidine) of the known sequence with a modified base such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other azo and deazo uracils, thymidines, cytosines, adenines, or guanines, 5-trifluoromethyl uracil and 5-trifluoro osine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule. For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose or (ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complementary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence, etc.

Some of the methods contemplated herein use nucleic acid molecules containing sequences encoding truncated non functional forms of TAP-1 or TAP-2, Truncated non functional forms of TAP-1 and TAP-2 may be constructed by deleting portions of the TAP-1 or TAP-2 gene to produce fragments. Such fragments should hybridize to the TAP-1 or TAP-2 sequences under stringent hybridization conditions. Stringent hybridization conditions are those which are stringent enough to provide specificity, reduce the number of mismatches, and yet are sufficiently flexible to allow formation of stable hybrids at an acceptable rate. Such conditions are known to those skilled in the art and are described, for example, in Sambrook, et al, (1989), *Molecular Cloning, A Laboratory Manual*, Cold Spring Harbor. The ability of the truncated forms of TAP-1 and TAP-2 to transport endogenous peptides may be determined using the methods described herein.

The invention also includes nucleic acid constructs containing both TAP-1 and TAP-2. In such case, the nucleic acid construct encodes a fusion protein of TAP-1 and TAP-2. The invention also includes TAP-1 or TAP-2 which have been modified in such a way as to decrease constitutively active phosphorylation regulated sites or peptide bridging sites or assembly structures.

Nucleic acid molecules having a sequence which codes for TAP-1 and TAP-2, including the homologs and modified forms discussed above, may be incorporated in a known manner into an appropriate expression vector which ensures good expression of the protein or a part thereof Possible expression vectors include but are not limited to cosmids, plasmids (including both naked DNA plasmids and liposome encapsulated plasmids), or modified viruses, so long as the vector is compatible with the target cell used.

It is contemplated that the nucleic acid molecules described herein contain the necessary elements for the transcription and translation of the inserted sequence. Suitable transcription and translation elements may be derived from a variety of sources, including bacterial, fungal, viral, mammalian, or insect genes. Selection of appropriate transcription and translation elements is dependent on the target cell chosen as discussed below, and may be readily accomplished by one of ordinary skill in the art. Examples of such elements include: a transcriptional promoter and enhancer or RNA polymerasc binding sequence, a ribosomal binding sequence, and a translation initiation signal. Additionally, depending on the host cell chosen and the vector employed, other genetic elements, such as an origin of replication, additional DNA restriction sites, enhancers, and sequences conferring inducibility of transcription may be incorporated into the expression vector. It will also be appreciated that the necessary transcriptional and translation elements may be supplied by the native TAP-1 gene, TAP-2 gene and/or their flanking regions.

The nucleic acid molecules may also contain a reporter gene which facilitates the selection of transformed or transfected host cells. Examples of reporter genes are genes encoding a protein such as β-galactosidase, chloramphenicol acetyltransferase, firefly luciferase, or an immunoglobulin or portion thereof such as the Fc portion of an immunoglobulin, preferably IgG. In a preferred embodiment, the reporter gene is Lac Z. Transcription of the reporter gene is monitored by changes in the concentration of the reporter protein such as β-galactosidase, chloramphenicol acetyltransferase, or firefly luciferase. This makes it possible to visualize and assay for expression of TAP.

Nucleic acid molecules comprising a sequence encoding TAP-1 or TAP-2 can be introduced into target cells via transformation, transfection, infection, electroporation, etc. Methods for transforming, transfecting, etc. host cells to express foreign DNA are well known in the art (see, e.g., Itakura et al., U.S. Pat. No. 4,704,362; Hinnen et al., *PNAS USA* 75:19291933, 1978; Murray et al., U.S. Pat. No. 4,801,542; Upshall et al., U.S. Pat. No. 4,935,349; Axel et al., U.S. Pat. No. 4,399,216; Goeddel et al., U.S. Pat. No. 4,784,950; Goeddel et al., U.S. Pat. No. 4,766,950; and Sambrook et al., *Molecular Cloning A Laboratory Manual, 2nd edition*, Cold Spring Harbor Laboratory Press, 1989; all of which are incorporated herein by reference in their entirety).

Suitable expression vectors for directing the expression in mammalian cells generally include a promoter, as well as other transcriptional and translational control sequences. Common promoters include SV40, MMTV, metallothionein-1, adenovirus Ela, CmV, immediate early, immunoglobulin heavy chain promoter and enhancer, and RSV-LTR. Protocols for the transfection of mammalian cells are well known to those of ordinary skill in the art.

The nucleic acid molecule encoding TAP is incorporated into a suitable vehicle for delivery to a cell such as viral vectors, plasmids, liposomes and microspheres. In a preferred embodiment, the nucleic acid molecule is introduced into the target call in a viral vector, preferably vaccine viral vectors, adenovirus based vectors, lenti virus based vectors and herpes simplex virus based vectors. The vectors may be live, attenuated, replication conditional or replication deficient. Most preferably the viral vectors are attenuated.

The present invention also includes pharmaceutical compositions or vaccines for carrying out the methods of the invention. Accordingly, the present invention provides a pharmaceutical composition for use in enhancing an immune response comprising an effective amount of an agent that can augment the level of a TAP molecule in admixture with a suitable diluent or carrier. In a preferred embodiment, the pharmaceutical composition comprises an effective amount of a nucleic acid molecule comprising a sequence encoding a TAP molecule in admixture with a suitable diluent or carrier.

The above described nucleic acid molecules encoding a TAP molecule or a vector comprising the nucleic acid molecules may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans and animals.

The pharmaceutical composition may be administered in a convenient manner as by injection (subcutaneous, intravenous, intraperitoneal, intramuscular, scarifacionally etc.), oral administration, inhalation, transdermal application, or rectal administration. Depending on the route of administration, the nucleic acid molecules may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985), or Handbook of Pharmaceutical Additives (compiled by Michael and Irene Ash, Gower Publishing Limited, Aldershot, England (1995)). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456, the pertinent disclosure of which is incorporated herein by reference in its entirety. As will also be appreciated by those skilled to the art, the administration of substances described herein may be by an inactive viral carrier.

The invention is further described and illustrated in the following examples which are not intended to limit the specifically enumerated embodiments or the scope of the appended claims. The pertinent portions of all cited references are incorporated herein in their entirety.

Materials and Methods

Animals, Cells and Viruses

The mouse strain C57BL/6 (H-2b) was obtained from Jackson Laboratories and housed and bred at the Biotechnology Breeding Facility (University of British Columbia). The mice were maintained according to the guidelines of the Canadian Council on Animal Care.

Mice were kept on a standard diet with water ad libitum. The colony was routinely screened for *Mycoplasma pulmonis*, and *Mycoplasma arthritidis*, rodent coronaviruses (including Hepatitis), and SV using the Murine ImmunoComb Test (Charles River Labs). The mice used in the experiments were between 6 and 12 weeks of age.

Recombinant vaccinia virus carrying human TAP-1 and TAP-2 genes (W-IiTAP-1,2) and carrying murine TAP-1 (VV-mTAP-1) were gifts from J. Yewdell, NIA, NIAID. Vaccinia virus encoding the plasmid PJS-5 (W-PJS-5), which was used as a negative control, was a gift from J. Alimonti, University of British Columbia, but is obtainable elsewhere or constructable by methods known to those of skill in the art. Vaccinia Virus Western Reserve strain (VV) was a gift from S. Gillam, University of British Columbia, but is available from scientific supply sources. VV strains were cultured on CV-I cells (ATCC). CV-I cells were cultured in DMEM/10% heat inactivated fetal bovine serum (FBS) (HyClone GIBCO BRL), 2 mM L-glutamine, 100 IU/ml penicillin, 100 Bg/ml streptomycin, 20 mM Hepes. RMA cells were cultured in RPMI/10% FBS, 2 mM L-glutamine, 100 IU/ml penicillin, 100 Bg/ml streptomycin, and 20 mM Hepes. VV titres were determined by tissue culture infective dose (TCID) assay or standard plaque assay (PFU) using Vero cells and CV-1 cells, respectively. T2 cells negative for both TAP-1 and TAP-2 were transfected with mouse K-2K$^b$ and stable clones were established with standard protocols.

Example 1

Mice were co-infected with a recombinant vaccinia virus carrying expressible TAP-I and TAP-2 genes (W-h TAP-1,2) and vaccinia viruses. The resultant cytotoxic T-lymphocyte activity was measured, and compared with controls. The resultant protection from lethal virus challenge was quantified.

The recombinant vaccinia virus containing TAP-I and TAP-2 genes (W-h TAP-1,2) and a control recombinant virus vaccinia containing no TAP genes (W-PJS-5) were prepared by standard methods outlined herein. Groups (n=3) of mice were vaccinated with equivalent does of VV-hTAP-1,2 or W-PJS-5, and, 12 days later, were challenged with a lethal dose of Vaccinia virus—WR (neurotropic strain) by the intranasal route. Mice were euthanized if weight loss fell to 75% of pre-challenge weight.

Figure 1:
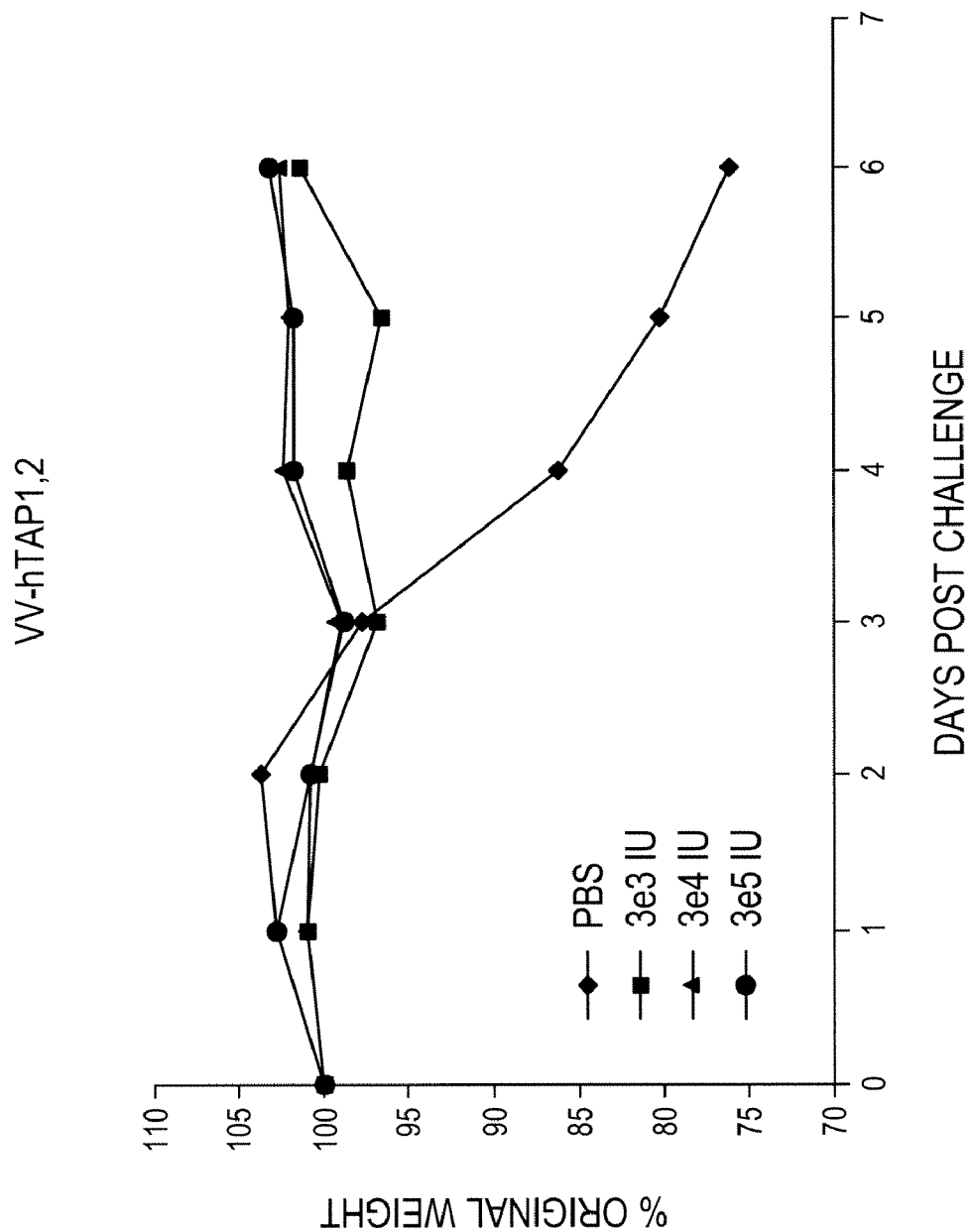
FIG. 1 and FIG. 2 are graphical representations of the results of experiments as shown in Example 1 below.

Three different dosages, $3\times10^3$ IU, $3\times10^4$ IU and $3\times10^5$ IU, of VV-h TAP-1,2 were administered to three different groups of animals. A fourth group received a sham vaccination with PBS. The results are presented graphically on FIG. 1 of the accompanying drawings. These graphs show that mice vaccinated with VVh TAP-1,2 were able to resist the challenge at all doses without morbidity, or mortality, compared with the animals receiving the sham vaccination.

Figure 2:
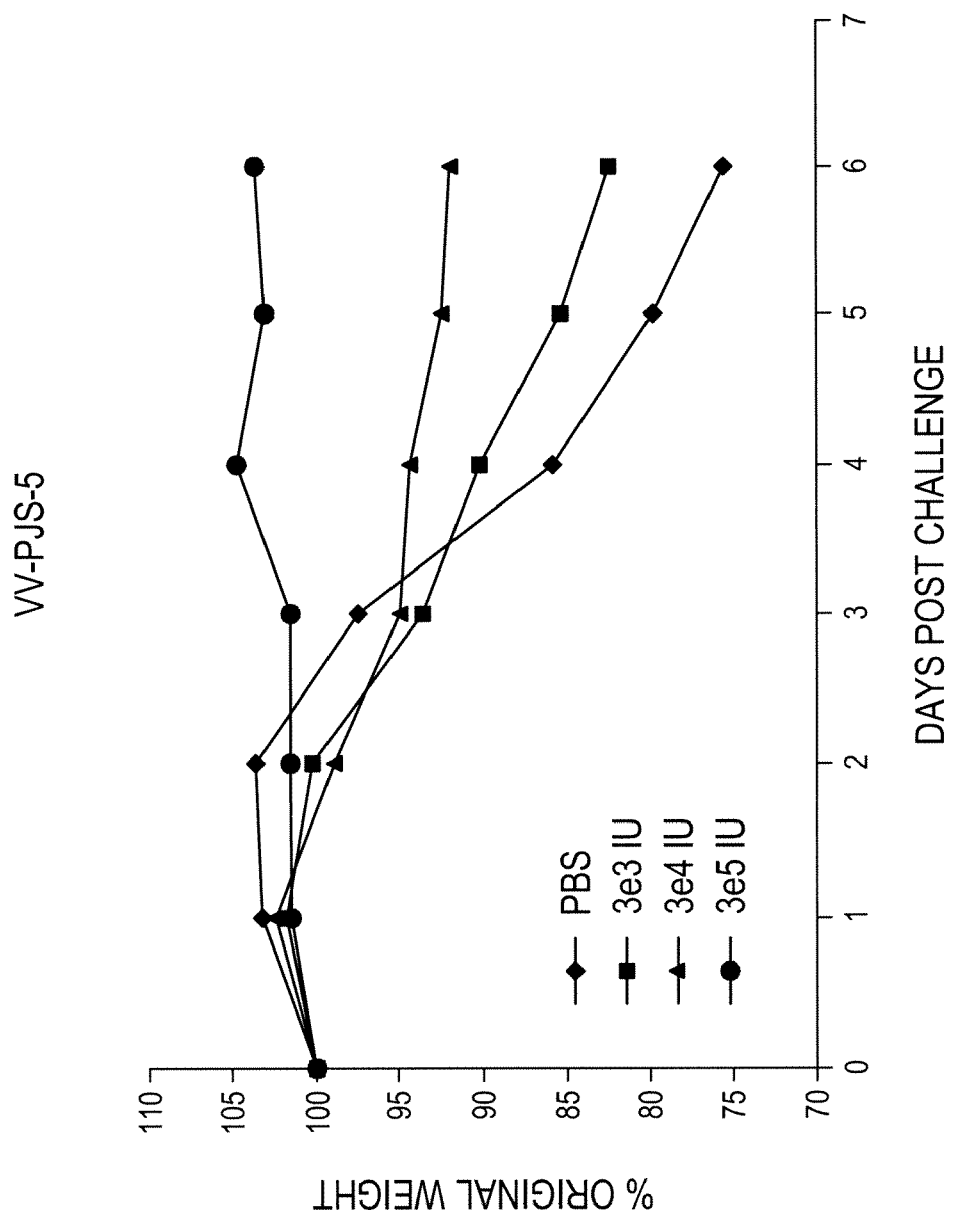
Figure 3:
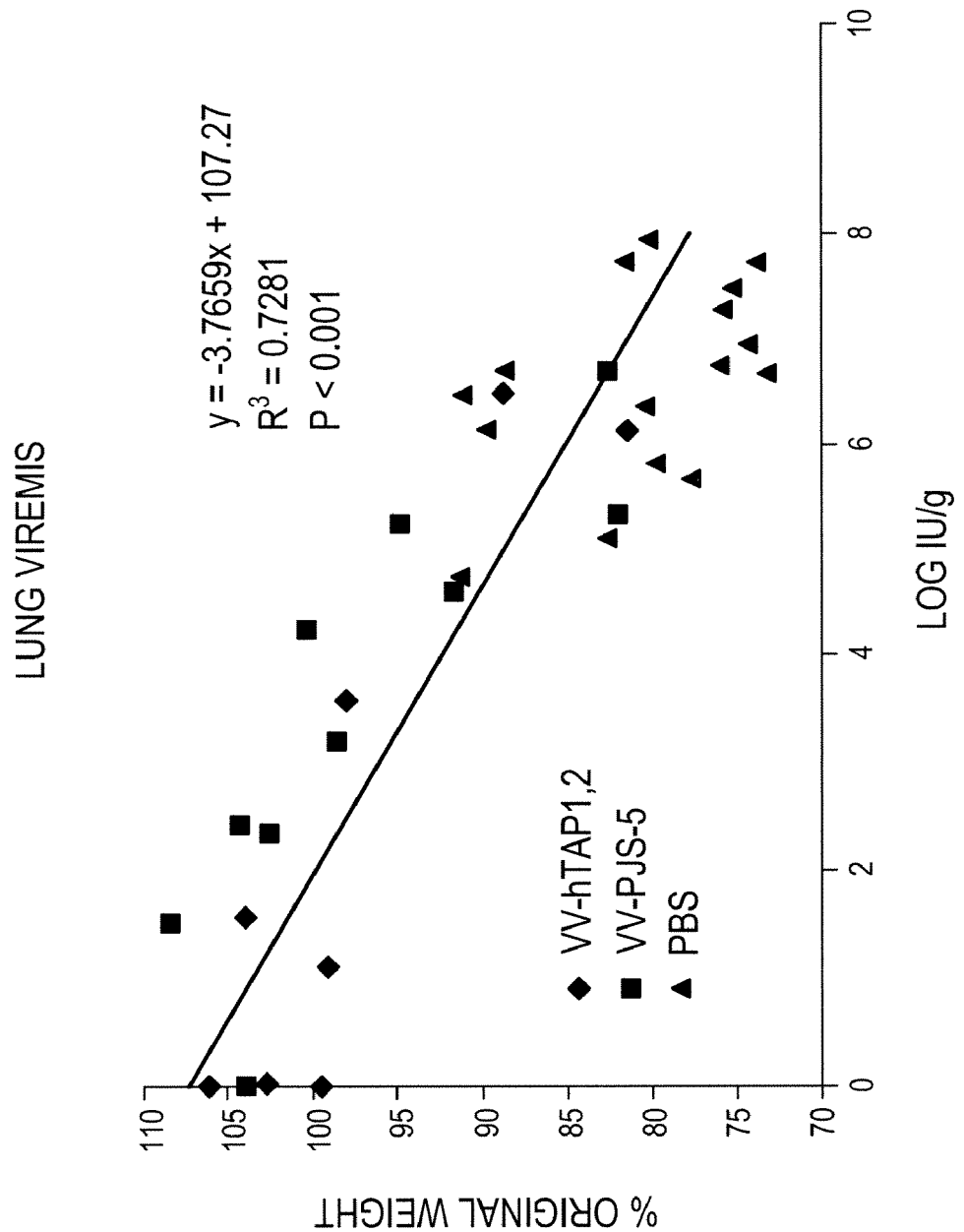
FIG. 3 is a graphical representation of the results of experiments shown in Example 2 below.
Figure 4:
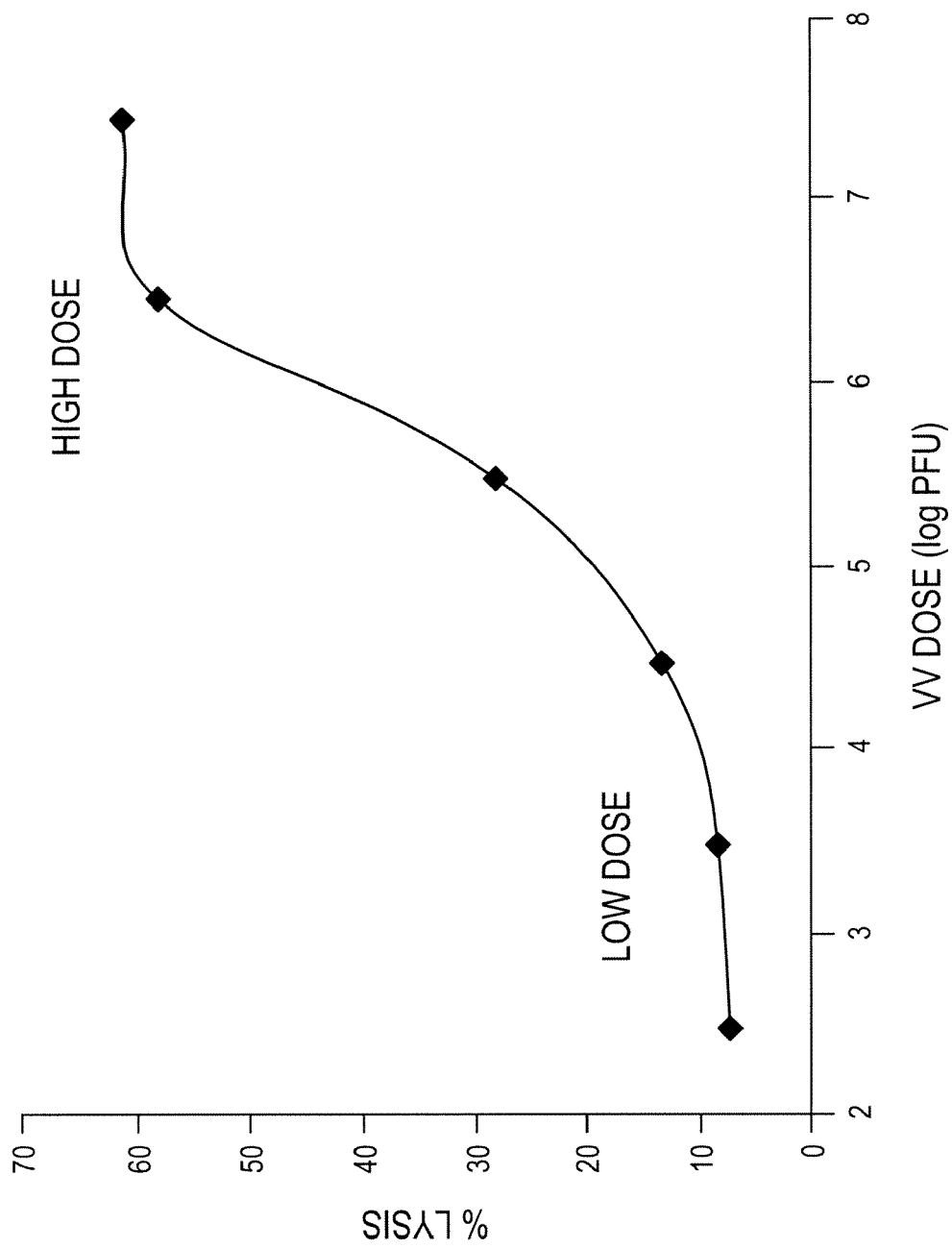
FIG. 4 and FIG. 5 are graphical representations of the results of experiments shown in Example 3 below.
Figure 5:
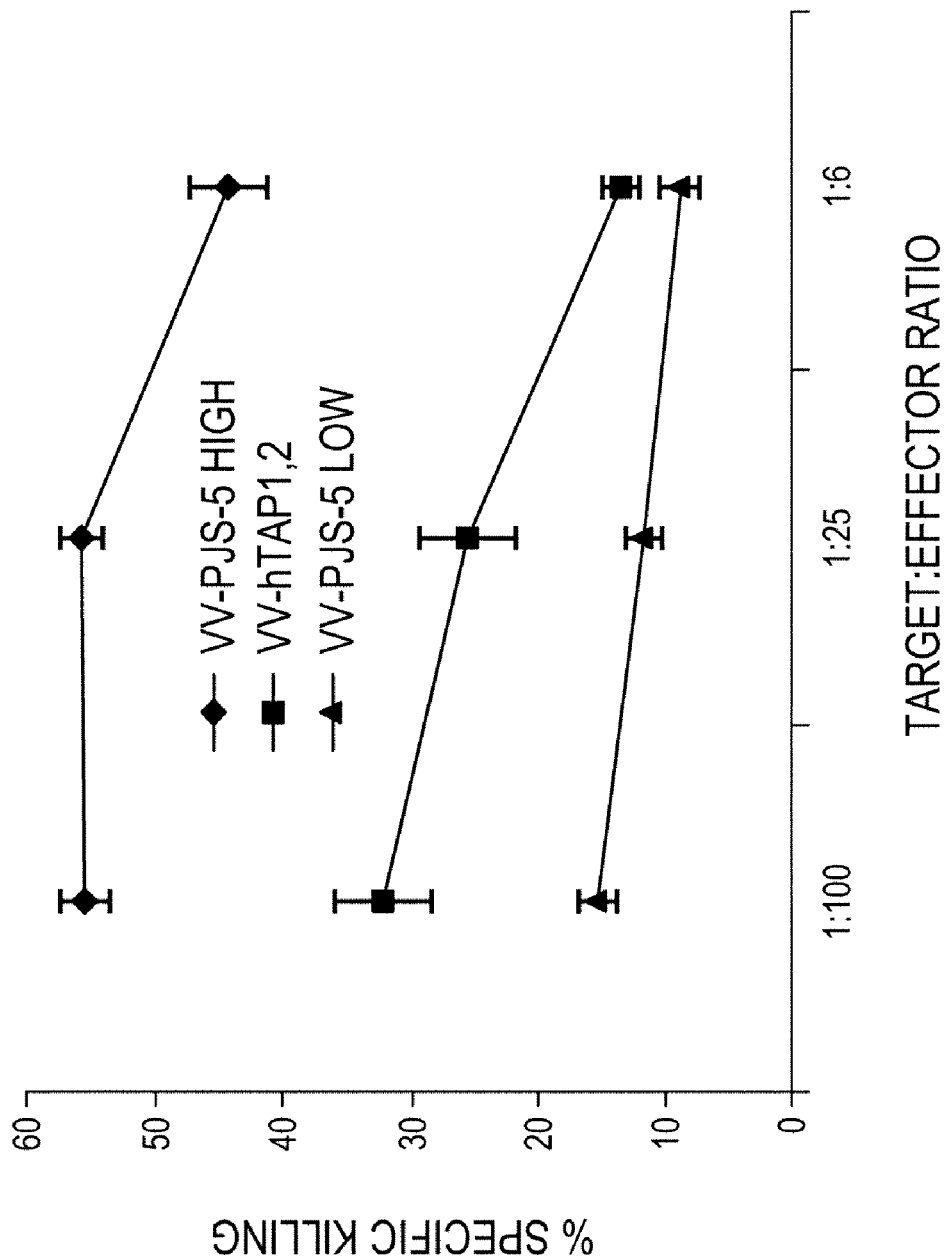
Figure 6:
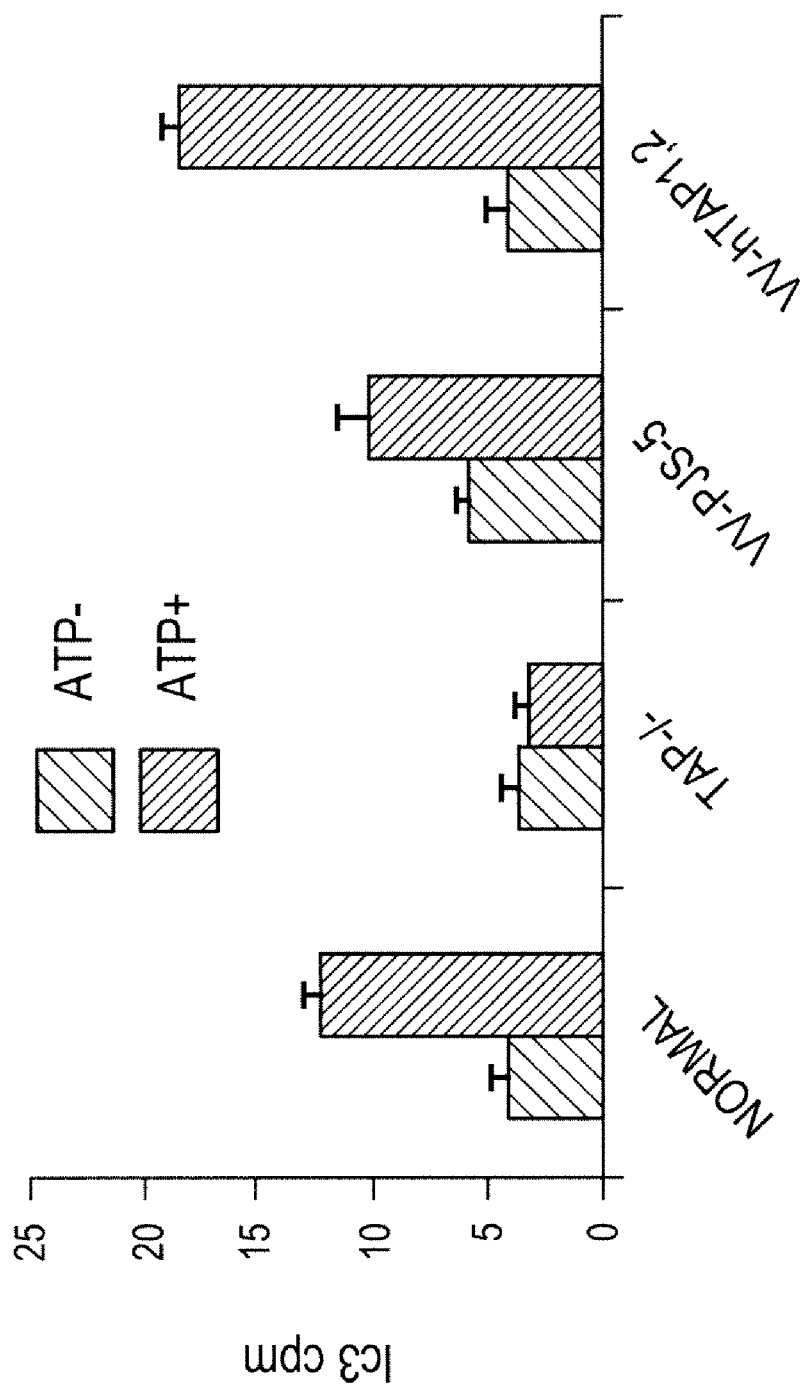
FIG. 6 is a graphical representation of the results of experiments shown in Example 4 below.

In a similar manner, three groups of control mice were vaccinated with the same three different does of VV-PJS-5 and similarly tracked. These results are presented graphically on accompanying FIG. 2 (along with the sham vaccination result from FIG. 1). Only at the highest vaccination doses were the mice able to resist the challenge without morbidity or mortality. It required 100× fold increase in vaccination dose of W-PJS-5 (3e5 IU) to generate the same protection as VV-h TAP-1,2 ($3\times10^3$ IU).

This experiment demonstrates that the recombinant W-hTAP-1,2 alone acts as an effective vaccine against *Pox viridae* infections subsequently encountered. Since it is more effective than the TAP-free VV-PJS-5 recombinant virus in this application, the extra effectiveness can be safely concluded to be due to the presence of TAP in the cells when the invading pox virus is subsequently encountered, not the viral vector alone.

Example 2

To confirm that weight loss was an adequate measure of resistance to the viral challenge, lung viremia (the presence of virus in the blood in the animal's lungs) and weight loss was determined 3 and 5 days after challenge with W-WR in groups of mice vaccinated with either PBS, VV-hTAP-1,2 ($3\times10^3$ IU) or VV-PJS-5 ($3\times lO^3$ IU). The results are presented graphically on accompanying FIG. 3. There was a highly significant correlation between weight loss and lung viremia.

Example 3

The infection doses required to generate minimal and maximal (CTL) responses against VV-PJS-5 was determined.

Cytotoxic T-cell activity in mice infected with VV is dependent on infection dose. Splenocytes from mice infected with doses of VV were assayed for their ability to kill cellular targets presenting MHC class 1 restricted VV antigens on their surface. A dose response titration curve is presented as FIG. 4 herein. Low infection doses do not stimulate W specific CTL activity. Maximal CTL activity was generated at high doses. Having determined the infectious doses required to generate minimal maximal CTL response against VV-PJ5-5 (a recombinant vaccinia virus not coding for TAP), the CTL activity was compared between mice infected with equivalent low doses of VV-h TAP-1,2 or W-PJS-5. The results are presented graphically on accompanying FIG. 5. The CTL activity in mice infected with VV-hTAP-1,2 was approximately two times greater than the activity generated by an equivalent low dose of W-PJS-5, indicating that the increases observed were specific to the presence of hTAP-1,2.

Example 4

A peptide translocation assay was used to measure the accumulation of radio-labeled peptides from the cytoplasm to the endoplasmic reticulum (ER). This is a measure of TAP activity. The presence or absence of ATP confirmed that the accumulation of peptide in the ER was due to active transport. The results are presented on FIG. 6, as bar graphs. Splenocytes from TAP knockout mice were unable to translocate peptides and confirmed that the observed accumulation was due to TAP activity. Peptide transport activity was higher in mice infected with VV-hTAP-1,2 than mice infected with W-PJS-5 or normal uninfected mice indicating that the increased activity was due to hTAP-1 expression.

Example 5

Histopathological examination of mice over expressing human TAP were conducted. Mice were randomized into three groups as follows: I-untreated, II-infected with VV-hTAP-1,2 ($3\times10^4$ IU), III-infected with W-PJS-5 ($3\times10^4$ IU). The mice in groups II and III were sacrificed on days 5, 15 and 30 after infection. The untreated mice (group I) were sacrificed five days following infection of groups I and II. Kidney, salivary gland, intestine, lung and joints were harvested from each mouse. Tissues were fixed in 10% formalin buffer and processed routinely for paraffin embedding. Fifteen sections from each tissue (spaced throughout the tissue sample) were cut and stained with hematoxylin and eosin. Histopathological alterations were assessed by an experienced blinded observer. Each tissue was examined for abnormal pathology as well as for inflammatory infiltrate.

Histopathological examination for evidence of autoimmune inflammation was performed in mice infected with VV-hTAP-1,2, W-PJS-5, or in uninfected mice. Kidney, salivary gland, intestine, lung and joints were graded for abnormal pathology and infiltrating leukocytes. The results are reported in the Table below. No differences were seen in the tissues of infected and uninfected mice over a thirty-day period post infection. Thus no evidence of enhanced inflammation or autoimmunity due to the over-expression of TAP was observed, and it can be safely concluded that TAP over-expression does not cause autoimmunity.

Table

TABLE 1

Pathology of Tissues from VV-PJS-5 and VV-hTAP-1,2

| Group | Lung | Tissue Examined Intestine | Joint | Kidney | Salivary Gland |
|---|---|---|---|---|---|
| Untreated | Normal | Normal | Normal | Normal | Normal |
| Day 30 VV-PJS-5 | Normal | Normal | Normal | Normal | Normal |
| Day 15 VV-hTAP-1,2 | Normal | Normal | Normal | Normal | Normal |
| Day 15 VV-PJS-5 | Normal | Normal | Normal | Normal | Normal |
| Day 15 VV-hTAP-1,2 | Normal | Normal | Normal | Normal | Normal |
| Day 30 VV-PJS-5 | Normal | Normal | Normal | Normal | Normal |
| Day 30 VV-hTAP-1,2 | Normal | Normal | Normal | Normal | Normal |

Note:
In the above Table, "Normal" is defined as no pathology or infiltrated leukocytes in the tissue tested.

Example 6

An experiment was conducted using laboratory mice to investigate the effect of TAP over expression in VV-infected cells, on W specific T-cell immune response. For the generation of W antigen specific effectors, mice were infected with infectious doses of W-hTAP-1,2 low dose ($1\times10^4$ PFU), W-PJS-5 low dose ($I\times IO^4$ PFU) or VV-PJS-5 high dose ($5\times10^6$ PFU). Six days after infection, splenocytes were removed and separated from erythrocytes and cultured and re-stimulated in vitro for 3 days with irradiated syngenic splenocytes infected with VV-PJS-5 ($3.4\times10^7$ PFO/$l\times IO^8$ syngenic splenocytes, MOI=0.335). To measure cytotoxic activity, a standard 4 hour $^{51}$Cr release assay was performed by using target RMA cells, infected overnight with W-PJS-5 (MOI=0.34). The targets were labeled with Na51CrO4 (70 BCi/10$^6$ cells) for 1 hr at 37° C. and then the standard 4 hour $^{51}$Cr release assay was performed. The cytotoxicity tests were done in 96 V-shaped well plates at many effector: target ratios.

Figure 7:
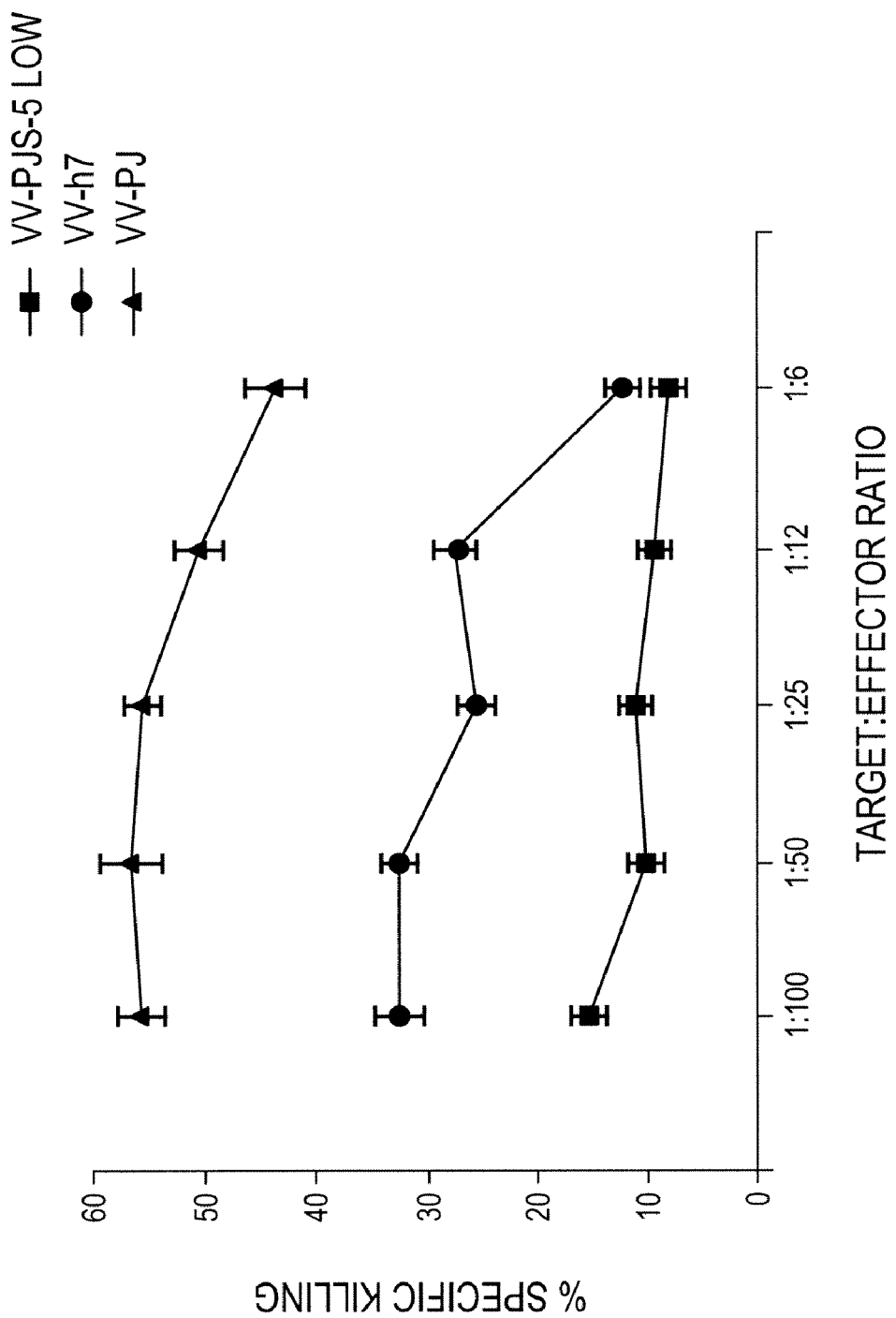
FIG. 7 is a graphical representation of the results of experiments shown in Example 5 below.

The dosages and results are presented graphically on accompanying FIG. 7. VV antigen specific activity of T-cells from the spleen of the mouse infected with W-hTAP1,2 (4×10$^3$ PFU) is substantially higher than the activity in mice infected with VV-PJS-5 (4×10$^3$ PFU) thereby confirming that greater T-cell responses against Poxviruses can be achieved by TAP over-expression. This observed enhancement of W specific cytotoxic activity is attributable to the increased activity of TAP.

Example 7

C57BL/6 naïve splenocytes were stimulated in vitro with 1 Bg/ml LPS for two days and then infected overnight with either VV-PJS-5 or W-hTAP-1,2 at two doses MOI=5×10$^4$ and MOI=0.25, respectively. The infected cells were then tested for total surface H-2K$^b$ expression and W-antigen associated H-2K$^b$ expression The results of the FACS analysis are presented on FIG. 8*a*, and show that the surface H-2 Kb expression does not differ between W-hTAP-1,2 and VV-PJS-5 infected splenocytes.

The results of a VV specific CTL assay, presented graphically as FIG. 8*b*, show increased killing of naïve splenocyte targets infected with VV-hTAP-1,2 compared with VV-PJS-5 infected targets.

It is thus shown that TAP over-expression in antigen presenting cells primes increased CTL activity by increasing VV specific MHC class 1 but not total MHC class 1 expression in splenocytes. This specificity towards VV indicates a particular and especially effective potential of the TAP augmentation approach to the development of *Pox viridae* vaccines and vaccine adjuvants, with special activity and lack of side effects in this application.

What is claimed is:

1. A pharmaceutical composition for administration to a living organism for the treatment or prophylaxis of Pox viridae infections, the composition comprising
    a Pox viridae viral antigen, and
    an adjuvant comprising a nucleic acid molecule containing expressible genes encoding TAP-1 and/or TAP-2, wherein the nucleic acid molecule is incorporated in a microsphere.

* * * * *